(12) United States Patent
Perloff et al.

(10) Patent No.: US 9,980,822 B2
(45) Date of Patent: May 29, 2018

(54) EXPANDABLE INTERBODY SPACER

(71) Applicant: GLOBUS MEDICAL, INC., Audubon, PA (US)

(72) Inventors: Jonathan Perloff, Slatington, PA (US); Christopher Saville, Morgantown, PA (US); Robert H. Wriggins, Tuckahoe, NJ (US)

(73) Assignee: Globus Medical, Inc., Audubon, PA (US)

( * ) Notice: Subject to any disclaimer, the term of this patent is extended or adjusted under 35 U.S.C. 154(b) by 0 days. days.

(21) Appl. No.: 14/697,981

(22) Filed: Apr. 28, 2015

(65) Prior Publication Data
US 2015/0238322 A1 Aug. 27, 2015

Related U.S. Application Data

(63) Continuation of application No. 13/483,852, filed on May 30, 2012, now Pat. No. 9,044,342.

(51) Int. Cl.
*A61F 2/44* (2006.01)
*A61F 2/46* (2006.01)
(Continued)

(52) U.S. Cl.
CPC ........ *A61F 2/4425* (2013.01); *A61B 17/7097* (2013.01); *A61F 2/442* (2013.01); *A61F 2/447* (2013.01); *A61F 2/4455* (2013.01); *A61F 2/4611* (2013.01); *A61F 2/44* (2013.01); *A61F 2002/2835* (2013.01); *A61F 2002/305* (2013.01); *A61F 2002/3037* (2013.01); *A61F 2002/3055* (2013.01); *A61F 2002/30108* (2013.01); *A61F 2002/30143* (2013.01); *A61F 2002/30156* (2013.01); *A61F 2002/30159* (2013.01); *A61F 2002/30166* (2013.01); *A61F 2002/30176* (2013.01); *A61F 2002/30189* (2013.01); *A61F 2002/30266* (2013.01);
(Continued)

(58) Field of Classification Search
CPC ....... A61F 2/442; A61F 2/4455; A61F 2/4611
USPC ........................................... 623/17.11–17.16
See application file for complete search history.

(56) References Cited

U.S. PATENT DOCUMENTS 5,171,278 A  12/1992  Pisharodi
5,545,229 A  8/1996  Parsons
(Continued)

*Primary Examiner* — Christopher Beccia

(57) ABSTRACT

The present invention relates to devices and methods for treating one or more damaged, diseased, or traumatized portions of the spine, including intervertebral discs, to reduce or eliminate associated back pain. In one or more embodiments, the present invention relates to an expandable interbody spacer. The expandable interbody spacer may comprise a first jointed arm comprising a plurality of links pivotally coupled end to end. The expandable interbody spacer further may comprise a second jointed arm comprising a plurality of links pivotally coupled end to end. The first jointed arm and the second jointed arm may be interconnected at a proximal end of the expandable interbody spacer. The first jointed arm and the second jointed arm may be interconnected at a distal end of the expandable interbody spacer. The first jointed arm and the second jointed arm may each be configured to fold inward in opposite directions to place the expandable interbody spacer in an expanded position.

20 Claims, 14 Drawing Sheets

(51) Int. Cl.
*A61B 17/70* (2006.01)
*A61F 2/30* (2006.01)
*A61F 2/28* (2006.01)

(52) U.S. Cl.
CPC .............. *A61F 2002/30364* (2013.01); *A61F 2002/30365* (2013.01); *A61F 2002/30405* (2013.01); *A61F 2002/30443* (2013.01); *A61F 2002/30462* (2013.01); *A61F 2002/30471* (2013.01); *A61F 2002/30472* (2013.01); *A61F 2002/30484* (2013.01); *A61F 2002/30492* (2013.01); *A61F 2002/30509* (2013.01); *A61F 2002/30515* (2013.01); *A61F 2002/30518* (2013.01); *A61F 2002/30525* (2013.01); *A61F 2002/30542* (2013.01); *A61F 2002/30545* (2013.01); *A61F 2002/30579* (2013.01); *A61F 2002/30581* (2013.01); *A61F 2002/30588* (2013.01); *A61F 2002/30629* (2013.01); *A61F 2002/30637* (2013.01); *A61F 2002/30772* (2013.01); *A61F 2002/30836* (2013.01); *A61F 2002/30892* (2013.01); *A61F 2002/30904* (2013.01); *A61F 2002/4415* (2013.01); *A61F 2002/4475* (2013.01); *A61F 2002/4627* (2013.01); *A61F 2002/4677* (2013.01); *A61F 2310/00017* (2013.01); *A61F 2310/00023* (2013.01); *A61F 2310/00179* (2013.01)

(56) References Cited

U.S. PATENT DOCUMENTS

| | | |
|---|---|---|
| 5,665,122 A | 9/1997 | Kambin |
| 5,693,100 A | 12/1997 | Pisharodi |
| 5,865,848 A | 2/1999 | Baker |
| 6,039,761 A * | 3/2000 | Li ........................ A61B 17/70 623/17.16 |
| 6,193,757 B1 | 2/2001 | Foley |
| 6,409,766 B1 | 6/2002 | Brett |
| 6,443,989 B1 | 9/2002 | Jackson |
| 6,454,807 B1 | 9/2002 | Jackson |
| 6,464,727 B1 | 10/2002 | Sharkey |
| 6,478,823 B1 | 11/2002 | Michelson |
| 6,572,653 B1 | 6/2003 | Simonson |
| 6,685,742 B1 | 2/2004 | Jackson |
| 6,695,882 B2 | 2/2004 | Bianchi |
| 6,719,794 B2 | 4/2004 | Gerber |
| 6,719,795 B1 | 4/2004 | Cornwell |
| 6,723,126 B1 | 4/2004 | Berry |
| 6,743,257 B2 | 6/2004 | Castro |
| 6,821,298 B1 | 11/2004 | Jackson |
| 6,833,006 B2 | 12/2004 | Foley |
| 6,835,206 B2 | 12/2004 | Jackson |
| 6,887,273 B2 | 5/2005 | Ralph |
| 6,893,464 B2 | 5/2005 | Kiester |
| 6,953,477 B2 | 10/2005 | Berry |
| 6,974,480 B2 | 12/2005 | Messerli |
| 7,018,413 B2 | 3/2006 | Kruger |
| 7,052,515 B2 | 5/2006 | Simonson |
| 7,074,239 B1 | 7/2006 | Cornwall |
| 7,087,055 B2 | 8/2006 | Lim |
| 7,094,257 B2 | 8/2006 | Mujwid |
| 7,223,291 B2 | 5/2007 | Errico |
| 7,223,292 B2 | 5/2007 | Messerli |
| 7,261,739 B2 | 8/2007 | Ralph |
| 7,270,680 B2 | 9/2007 | Ralph |
| 7,273,498 B2 | 9/2007 | Bianchi |
| 7,513,900 B2 | 4/2009 | Carrison |
| 7,655,042 B2 | 2/2010 | Foley et al. |
| 7,763,074 B2 | 7/2010 | Altarac |
| 7,942,905 B2 * | 5/2011 | Lim .................. A61B 17/7007 606/246 |
| 2003/0236520 A1 | 12/2003 | Lim |
| 2004/0102774 A1 | 5/2004 | Trieu |
| 2004/0102847 A1 | 5/2004 | Sato |
| 2005/0070911 A1 | 3/2005 | Carrison |
| 2006/0089642 A1 | 4/2006 | Diaz |
| 2006/0224241 A1 | 10/2006 | Butler |
| 2006/0241643 A1 | 10/2006 | Lim et al. |
| 2007/0093899 A1 | 4/2007 | Dutoit |
| 2008/0243255 A1 * | 10/2008 | Butler .................. A61F 2/4465 623/17.16 |
| 2009/0222100 A1 * | 9/2009 | Cipoletti ................ A61F 2/447 623/17.16 |
| 2010/0174373 A1 * | 7/2010 | Galley ............... A61B 17/7065 623/17.13 |
| 2010/0222816 A1 | 9/2010 | Gabelberger et al. |
| 2011/0282459 A1 | 11/2011 | McClellan, III et al. |
| 2011/0295370 A1 | 12/2011 | Suh |
| 2012/0004732 A1 | 1/2012 | Goel |
| 2012/0123546 A1 * | 5/2012 | Medina ................ A61F 2/442 623/17.16 |
| 2012/0209386 A1 * | 8/2012 | Triplett ................ A61F 2/4465 623/17.16 |
| 2012/0245639 A1 | 9/2012 | Dwyer |
| 2012/0245696 A1 | 9/2012 | Thibodeau |
| 2012/0296379 A1 | 11/2012 | Moraney-Meister |
| 2012/0296430 A1 | 11/2012 | Edie |
| 2012/0296431 A1 | 11/2012 | Kim |
| 2012/0310287 A1 | 12/2012 | Bao |
| 2013/0110248 A1 * | 5/2013 | Zipnick ................ A61F 2/4455 623/17.16 |

* cited by examiner

EXPANDABLE INTERBODY SPACER

REFERENCE TO RELATED APPLICATIONS

The present application is a continuation application of U.S. patent application Ser. No. 13/483,852, filed May 30, 2012, which is entitled "Expandable Interbody Spacer." The entire contents of the application are hereby incorporated by reference in its entirety.

FIELD OF THE INVENTION

The present invention relates to devices and methods for treating one or more damaged, diseased, or traumatized portions of the spine, including intervertebral discs, to reduce or eliminate associated back pain. In one or more embodiments, the present invention relates to an expandable interbody spacer.

BACKGROUND OF THE INVENTION

The vertebrate spine is the axis of the skeleton providing structural support for the other body parts. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation.

The typical vertebra has a thick anterior bone mass called the vertebral body, with a neural (vertebral) arch that arises from the posterior surface of the vertebral body. The central of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc.

The spinal disc and/or vertebral bodies may be displaced or damaged due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant, which may be referred to as an interbody spacer, can be inserted into the cavity created where the intervertebral disc was removed to help maintain height of the spine and/or restore stability to the spine. An example of an interbody spacer that has been commonly used is a cage, which typically is packed with bone and/or bone-growth-inducing materials. However, there are drawbacks associated with conventional interbody spacers, such as cages and other designs. For instances, conventional interbody spacers may be too large and bulky for introduction into the disc space in a minimally invasive manner, such as may be utilized in a posterior approach. Further, these conventional interbody spacers may have inadequate surface area contact with the adjacent endplates if sized for introduction into the disc space in a minimally invasive manner. In addition, conventional interbody spacers designed for introduction into the disc space in a minimally invasive manner may lack sufficient space for packing of bone-growth-inducing material, thus potentially not promoting the desired graft between the adjacent endplates.

Therefore, a need exists for an interbody spacer that can be introduced in a minimally manner that provides a desired amount of surface area contact with the adjacent endplates and has an increased space for packing of bone-growth-inducing material.

SUMMARY OF THE INVENTION

The present invention relates to an expandable interbody spacer. The expandable interbody spacer may comprise a first jointed arm comprising a plurality of links pivotally coupled end to end. The expandable interbody spacer further may comprise a second jointed arm comprising a plurality of links pivotally coupled end to end. The first jointed arm and the second jointed arm may be interconnected at a proximal end of the expandable interbody spacer. The first jointed arm and the second jointed arm may be interconnected at a distal end of the expandable interbody spacer. The first jointed arm and the second jointed arm may each be configured to fold inward in opposite directions to place the expandable interbody spacer in an expanded position.

BRIEF DESCRIPTION OF THE DRAWINGS

The present invention will be more readily understood with reference to the embodiments thereof illustrated in the attached drawing figures, in which.

Throughout the drawing figures, it should be understood that like numerals refer to like features and structures.

DETAILED DESCRIPTION OF THE INVENTION

Figure 1:
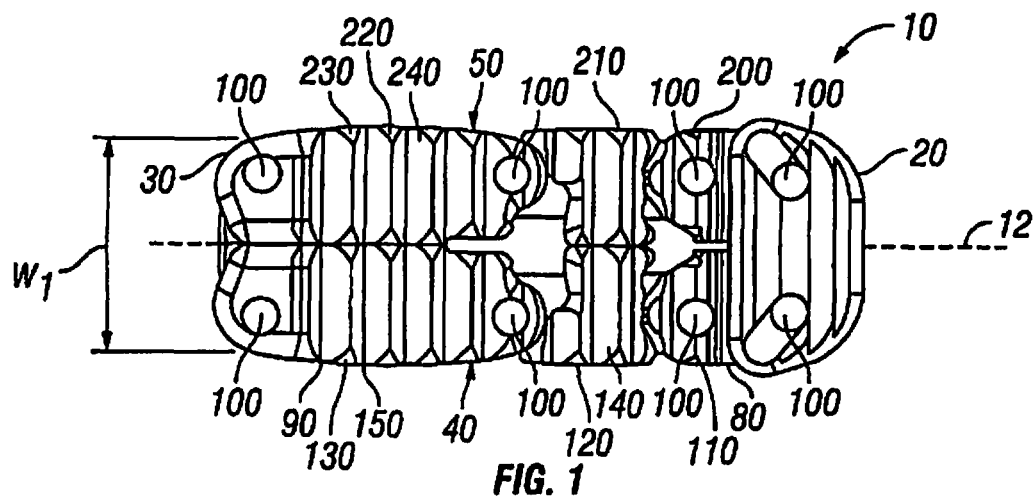
FIG. 1 is a top view of an expandable interbody spacer shown in a collapsed position in accordance with embodiments of the present invention.
Figure 2:
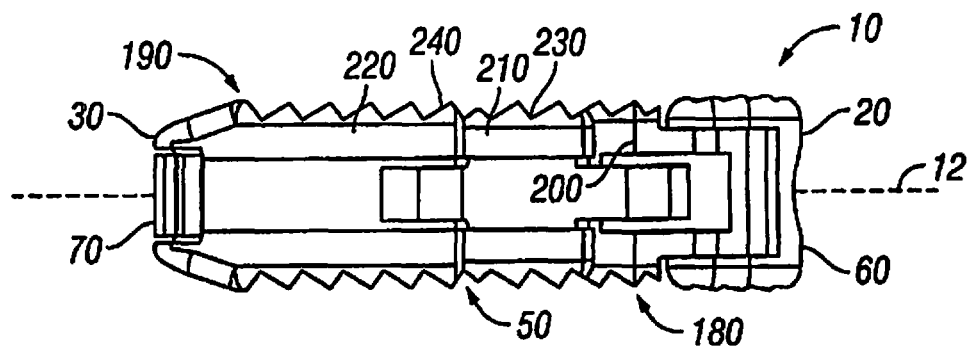
FIG. 2 is a side view of the expandable interbody spacer of FIG. 1 shown in a collapsed position.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-10, an expandable interbody spacer 10 is shown in accordance with embodiments of the present invention. In the illustrated embodiment, the expandable interbody spacer 10 has a proximal end 20 and a distal end 30. The expandable interbody spacer 10 may include a first jointed arm 40 and a second jointed arm 50 positioned on either side of longitudinal axis 15 of the spacer 10. The first and second jointed arms 40, 50 may be interconnected at the proximal end 20, for example, by a proximal connection member 60. The first and second jointed arms 40, 50 may be interconnected at the distal end 30, for example, by a distal connection member 70. The first and second jointed arms 40, 50 The expandable interbody spacer 10 may be made from a number of materials, including titanium, stainless steel, titanium alloys, non-titanium alloys, polymeric materials, plastic composites, polyether ether ketone ("PEEK") plastic material, ceramic, elastic materials, and combinations thereof. While the expandable interbody spacer 10 may be used with a posterior, anterior, lateral, or combined approach to the surgical site, the spacer 10 may be particularly suited with a posterior approach.

The first jointed arm 40 has a proximal end 80 and a distal end 90. The proximal end 80 may be pivotally coupled to the proximal connection member 60. The distal end 90 may be pivotally coupled to the distal connection member 70. Any of a variety of different fasteners may be used to pivotally couple the proximal end 80 and the distal end 90 and the proximal connection member 60 and the distal connection member 70, such as pins 100, for example. In another embodiment (not illustrated), the connection may be a hinged connection. As illustrated, the first jointed arm 40 may comprise a plurality of links that are pivotally coupled to one another. In the illustrated embodiment, the first jointed arm 40 comprises first link 110, second link 120, and third link 130. When the spacer 10 is in a collapsed position, the first link 110, second link 120, and third link may be generally axially aligned. As illustrated, the first link 110, second link 120, and third link 130 may be connected end to end. When the spacer 10 is in a collapsed position, the first link 110, second link 120, and third link 130 may be generally axially aligned. The first link 110 and the second link 120 may be pivotally coupled, and the second link 120 and the third link 130 may also be rotatably coupled. Any of a variety of different fasteners may be used to pivotally couple the links 110, 120, 130, such as pins 100, for example. In another embodiment (not illustrated), the coupling may be via a hinged connection.

As best seen in FIGS. 1, 5-7, 9, and 10, an upper surface 140 of the first jointed arm 40 may be defined by the links 110, 120, 130. The upper surface 140 should allow for engagement of the first jointed arm 40 with one of the adjacent vertebral bodies. In some embodiments, the upper surface 140 may include texturing 150 to aid in gripping the adjacent vertebral bodies. Although not limited to the following, the texturing 150 can include teeth, ridges, friction-increasing elements, keels, or gripping or purchasing projections.

Figure 7:
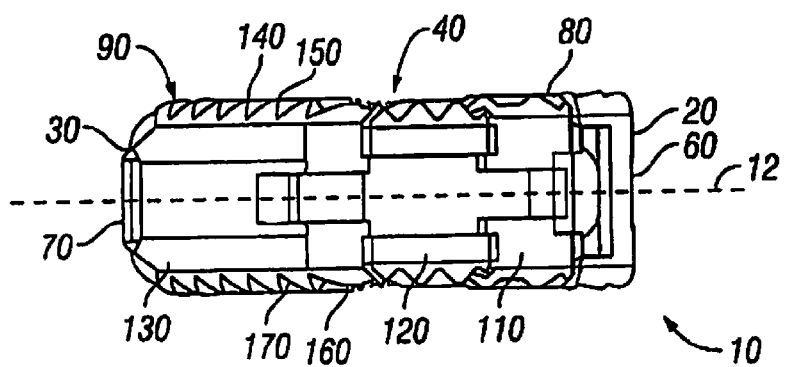
FIG. 7 is a right side view of the expandable interbody spacer of FIG. 1 shown in an expanded position.
Figure 9:
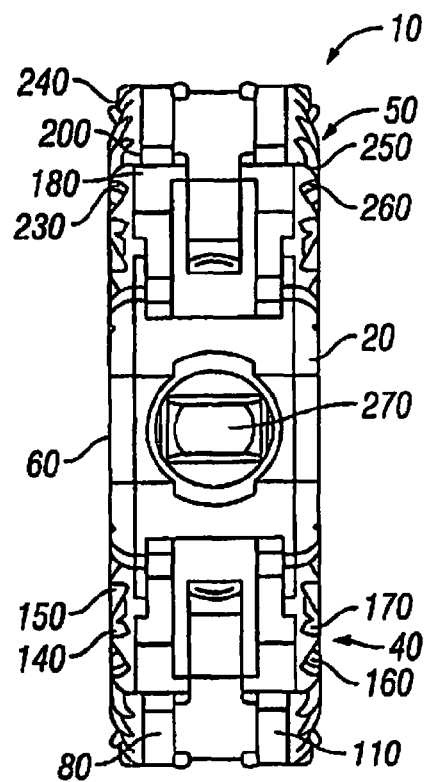
FIG. 9 is a proximal end view of the expandable interbody spacer of FIG. 1 shown in an expanded position.
Figure 10:
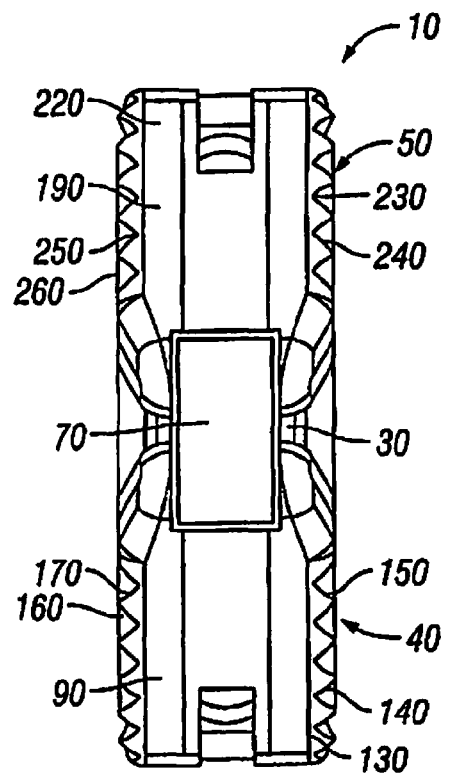
FIG. 10 is a distal end view of the expandable interbody spacer of FIG. 1 shown in an expanded position.

As best seen in FIGS. 7, 9, and 10 a lower surface 160 of the first jointed arm 40 may be defined by the links 110, 120, 130. The lower surface 160 should allow for engagement of the first jointed arm 40 with one of the adjacent vertebral bodies. In some embodiments, the lower surface 160 may include texturing 170 to aid in gripping the adjacent vertebral bodies. Although not limited to the following, the texturing 170 can include teeth, ridges, friction-increasing elements, keels, or gripping or purchasing projections.

The second jointed arm 50 has a proximal end 180 and a distal end 190. The proximal end 180 may be pivotally coupled to the distal connection member 70. The distal end 190 may be pivotally coupled to the distal connection member 70. Any of a variety of different fasteners may be used to pivotally couple the proximal end 180 and the distal end 190 and the proximal connection member 60 and the distal connection member 70, such as pins 100, for example. In another embodiment (not illustrated), the connection may be a hinged connection. As illustrated, the second jointed arm 50 may comprise a plurality of links that are pivotally coupled to one another. In the illustrated embodiment, the second jointed arm 50 comprises first link 200, second link 210, and third link 220. When the spacer 10 is in a collapsed position, the first link 200, second link 210, and third link 220 may be generally axially aligned. As illustrated, the first link 200, second link 210, and third link 220 may be connected end to end. The first link 200 and the second link 210 may be pivotally coupled, and the second link 210 and the third link 220 may also be pivotally coupled. Any of a variety of different fasteners may be used to pivotally couple the links 200, 210, 220, such as pins 100, for example. In another embodiment (not illustrated), the coupling may be via a hinged connection.

As best seen in FIGS. 1, 2, 6, and 8-10, an upper surface 230 of the second jointed arm 50 may be defined by the links 200, 210, 220. The upper surface 230 should allow for engagement of the second jointed arm 50 with one of the adjacent vertebral bodies. In some embodiments, the upper surface 230 may include texturing 240 to aid in gripping the adjacent vertebral bodies. Although not limited to the following, the texturing 240 can include teeth, ridges, friction-increasing elements, keels, or gripping or purchasing projections.

Figure 8:
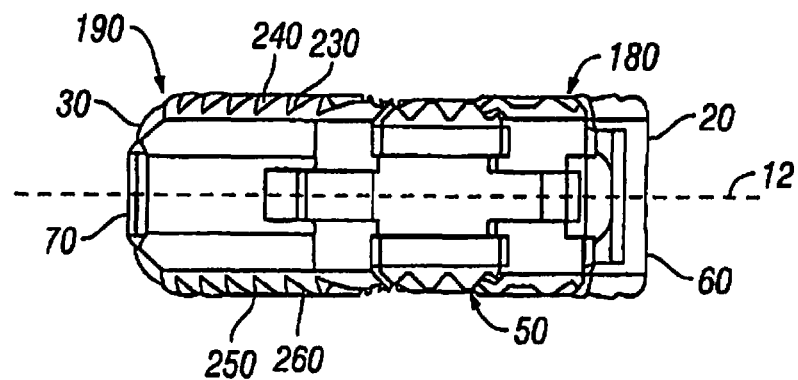
FIG. 8 is a left side view of the expandable interbody spacer of FIG. 1 shown in an expanded position.

As best seen in FIGS. 8-10, a lower surface 250 of the second jointed arm 50 may be defined by the links 200, 210, and 220. The lower surface 250 should allow for engagement of the second jointed arm 50 with one of the adjacent vertebral bodies. In some embodiments, the lower surface 250 may include texturing 260 to aid in gripping the adjacent vertebral bodies. Although not limited to the following, the texturing 260 can include teeth, ridges, friction-increasing elements, keels, or gripping or purchasing projections.

Figure 3:
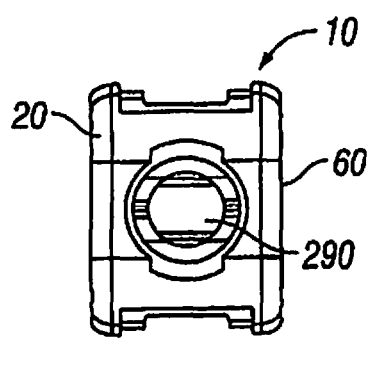
FIG. 3 is a proximal end view of the expandable interbody spacer of FIG. 1 shown in a collapsed position.
Figure 4:
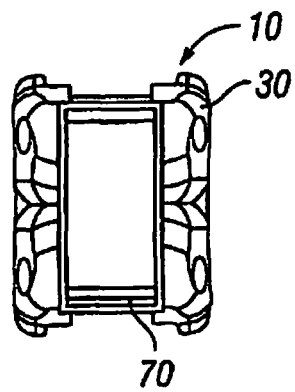
FIG. 4 is a distal end view of the expandable interbody spacer of FIG. 1 shown in a collapsed position.
Figure 5:
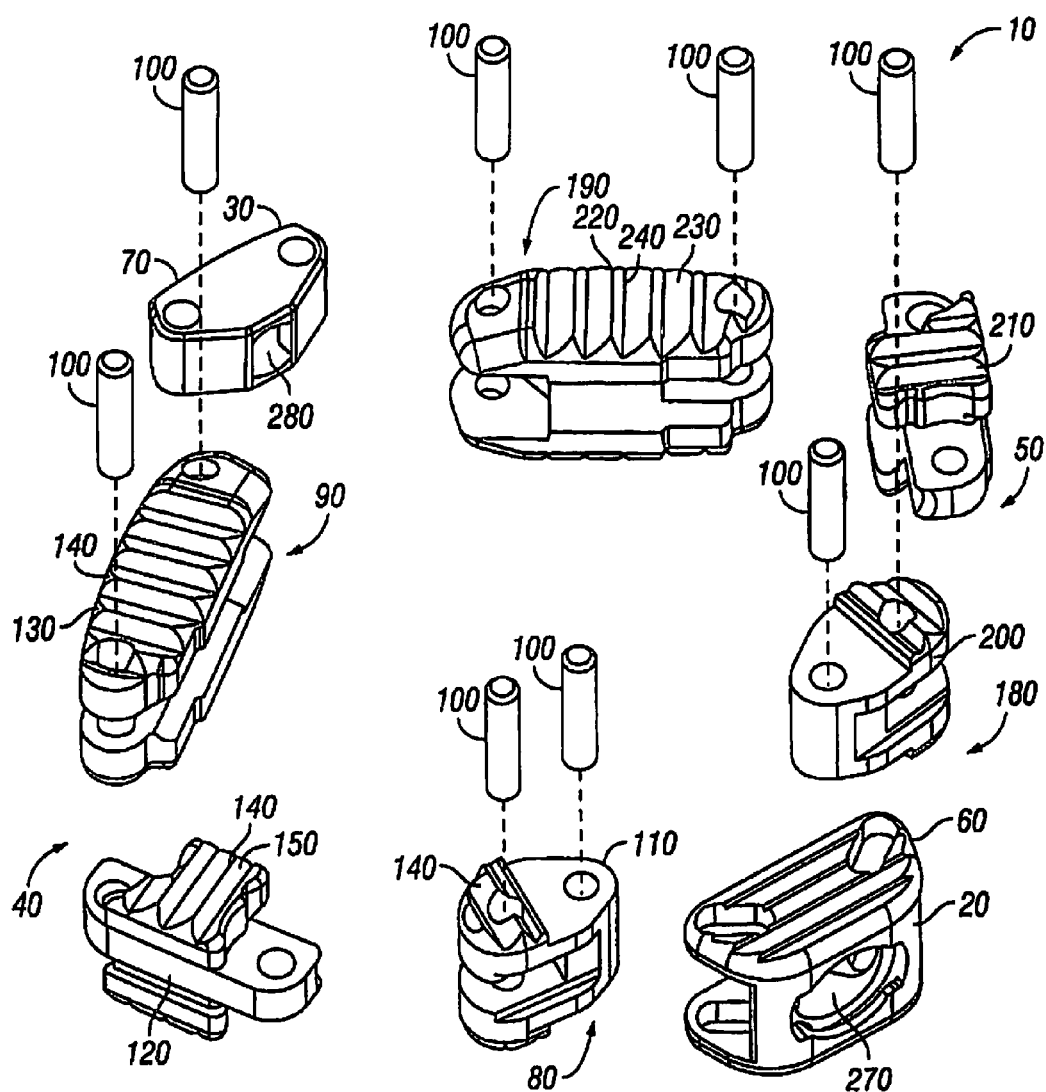
FIG. 5 is an exploded view of the expandable interbody spacer of FIG. 1.

With reference now to FIGS. 3, 5, and 9, a bore 270 extends through proximal connection end 60. The bore 270 may extend generally parallel to the longitudinal axis 12 (see FIG. 1) of the spacer 10. The first jointed arm 40 and the second jointed arm 50 may define a hollow interior portion (not shown) that extends axially through the spacer 10. The bore 270 in the proximal connection end 60 may communicate with this hollow interior portion. As best shown on FIG. 5, the distal connection end 70 may include an opening 280. As illustrated, the opening 280 may face inward and may not extend all the way through the distal connection 70. In one embodiment, the opening 280 may be generally aligned with the bore 270 in the proximal connection end 60 such a tool (e.g., tool 340 shown on FIG. 12) inserted into the bore 270 may be received in the opening 280 for placement of the spacer 10 into a disc space and/or expansion of the spacer 10.

FIGS. 1-4 illustrate the expandable interbody spacer 10 in a collapsed position. In accordance with present embodiments, the expandable interbody spacer 10 may be laterally expanded to an expanded position. FIGS. 6-10 illustrate the expandable interbody spacer 10 in an expanded position. In the expanded position, the first arm 40 and the second arm 50 have each been folded inward in opposite directions. For example, the proximal end 80 and the distal end 90 of the first arm 40 may be folded closer together. The links 110, 120, 130 should pivot with respect to one another when the first arm 40 is folded inward. The proximal end 80 should pivot at the proximal connection end 60, and the distal end 90 should pivot at the distal connection end 70. By way of further example, the proximal end 180 and the distal end 190 of the second arm 50 may also be folded together. The links 200, 210, 220 should pivot with respect to another when the second arm is folded inward. The proximal end 180 should pivot at proximal connection end 60, and the distal end 190 should pivot at the distal connection end 70. After placement in the expanded position, the expandable interbody spacer 10 can be secured in the expanded position to prevent collapse of the expandable interbody spacer 10 upon application of spacer. Any of a variety of different techniques may be used to secure the expandable interbody spacer 10, including pins or other suitable locking mechanism, for example.

Figure 6:
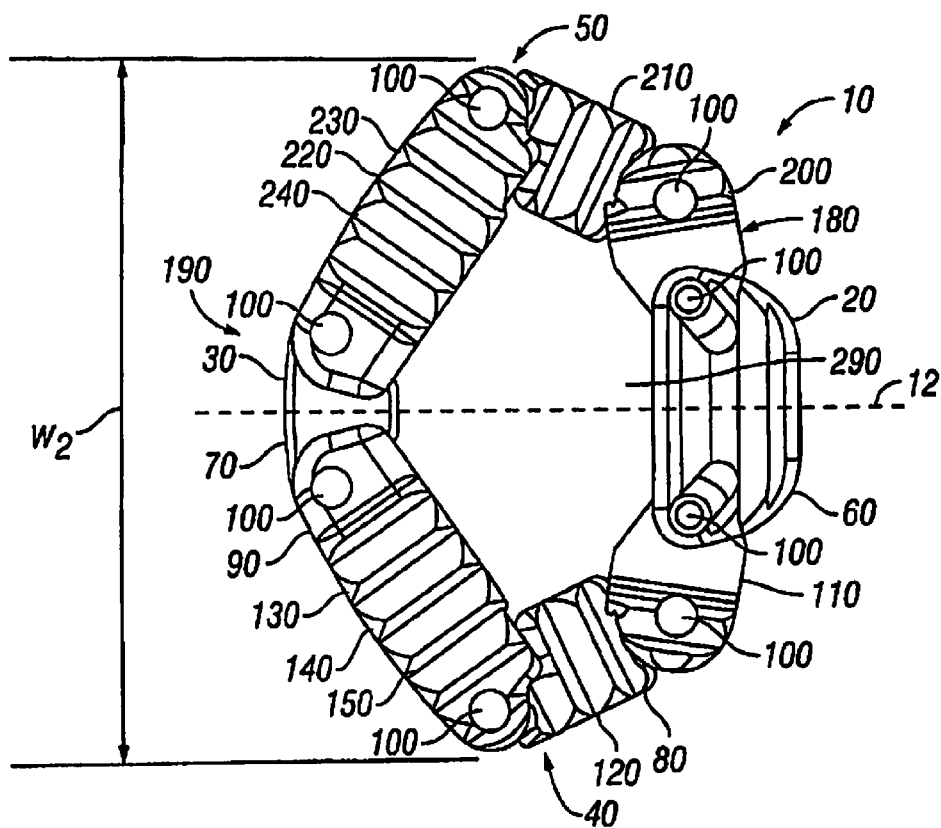
FIG. 6 is a top view of the expandable interbody spacer of FIG. 1 shown in an expanded position.

As illustrated by FIG. 6, the first and second jointed arms 40, 50 define an interior cavity 290 when in an expanded position. The interior cavity 290 may be filled with a bone-growth-inducing material, such as bone material, bone-growth factors, or bone morphogenic proteins. As will be appreciated by those of ordinary skill in the art, the bone-growth-inducing material should induce the growth of bone material, thus promoting fusion of the adjacent vertebra.

The expandable interbody spacer 10 may be sized to accommodate different applications, different procedures, implantation into different regions of the spine, or size of disc space. For example, the expandable interbody spacer 10 may have a width W1 (as shown on FIG. 1) prior to expansion of about 8 to about 22 and alternatively from about 10 to about 13. By way of further example, the expandable interbody spacer 10 may be expanded to a width W2 (as shown on FIG. 6) in a range of about 26 to about 42 and alternatively from about 16 to about 32. It should be understood that the width W1 or W2 whether prior to, or after, expansion generally refers to the width of the expandable interbody spacer 10 extending transverse to the longitudinal axis 12 of the spacer 10. In general, the width W2 of the expandable interbody spacer 10 after expansion should be greater than the width W1 of the expandable interbody spacer 10 prior to expansion.

Figure 11:
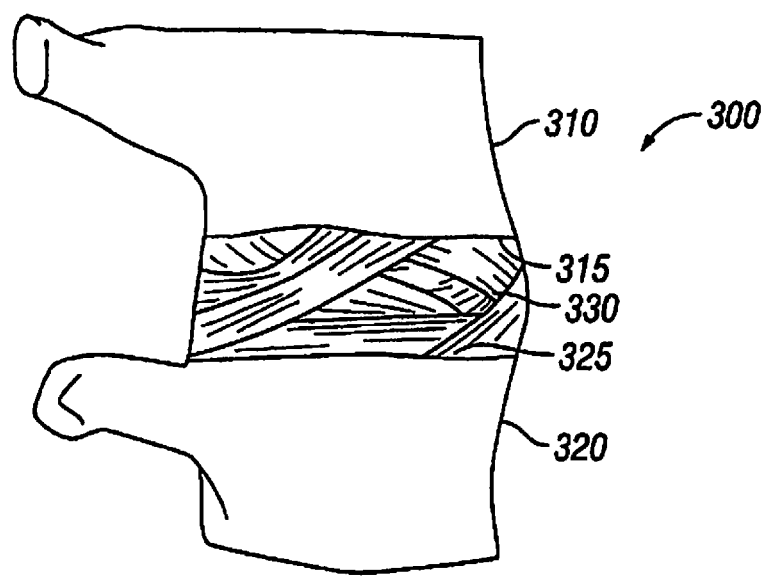
FIG. 11 is a view showing disc space between adjacent vertebrae in accordance with embodiments of the present invention.
Figure 12:
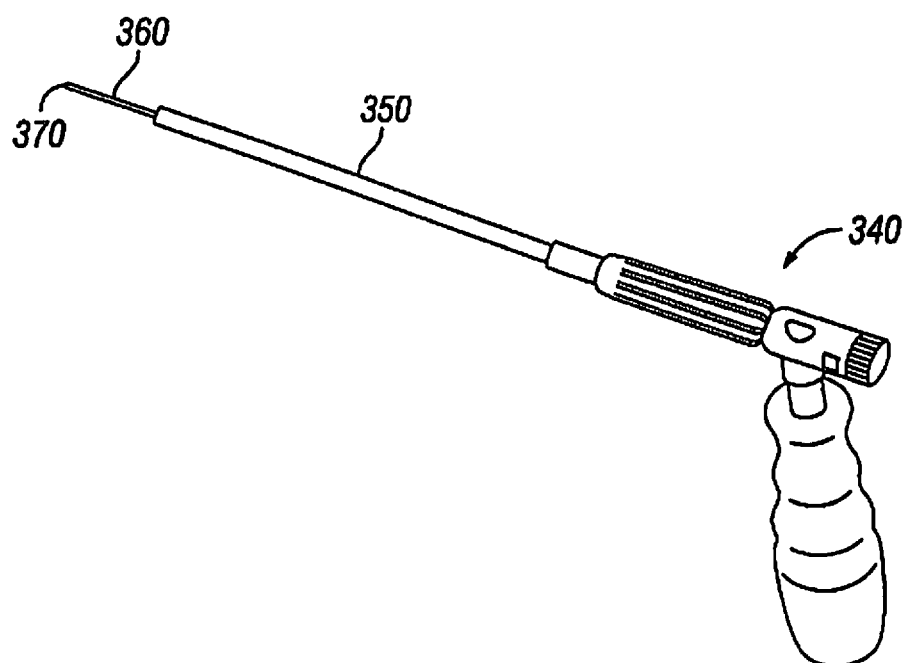
FIG. 12 is a view of a tool for insertion of an expandable interbody spacer in accordance with embodiments of the present invention.

In accordance with present embodiments, the expandable interbody spacer 10 may be used in the treatment of damage or disease of the vertebral column. In one embodiment, the expandable interbody spacer 10 may be inserted into a disc space between adjacent vertebrae in which the intervertebral disc has been partially or completely removed. FIG. 11 illustrates a spinal segment 300 into which the expandable interbody spacer 10 (e.g., FIGS. 1-10) may be inserted. The spinal segment 300 includes adjacent vertebrae, identified by reference numbers 310 and 320. Each of the adjacent vertebrae 310, 320 has a corresponding endplate 315, 325. The disc space 330 is the space between the adjacent vertebrae 310, 320. FIG. 12 illustrates a tool 340 that may be used in the insertion of the expandable interbody spacer 10 into the disc space 330. The tool 340 includes a shaft 350 having an elongated end portion 360 for coupling to the expandable interbody spacer 10. The elongated end portion 360 has a distal tip 370.

Figure 13:
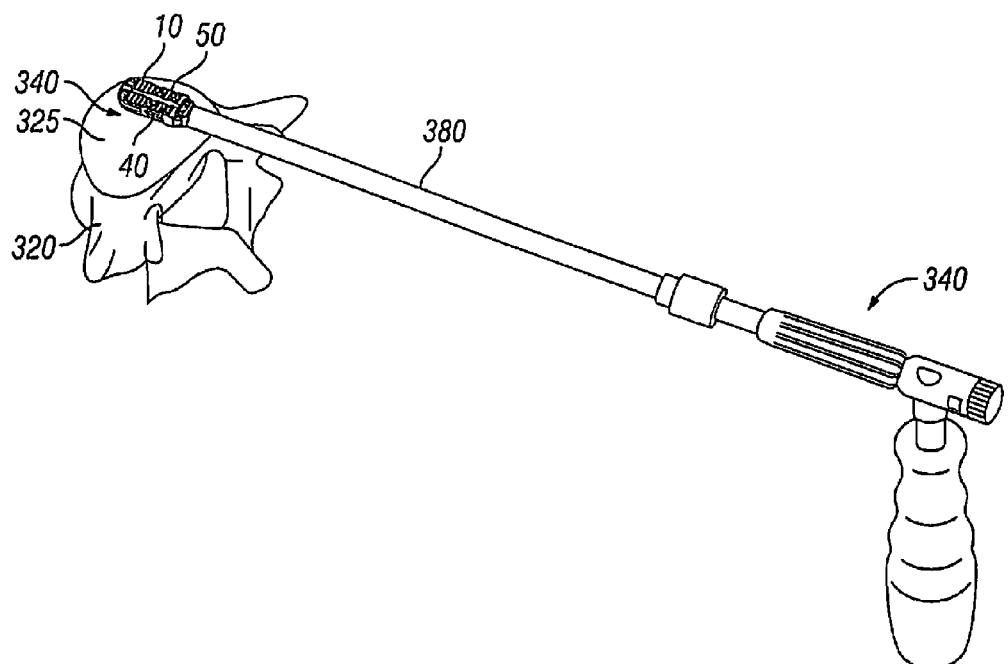
FIG. 13 is a view showing the tool of FIG. 12 introducing an expandable interbody spacer into a disc space in a collapsed position in accordance with embodiments of the present invention.
Figure 14:
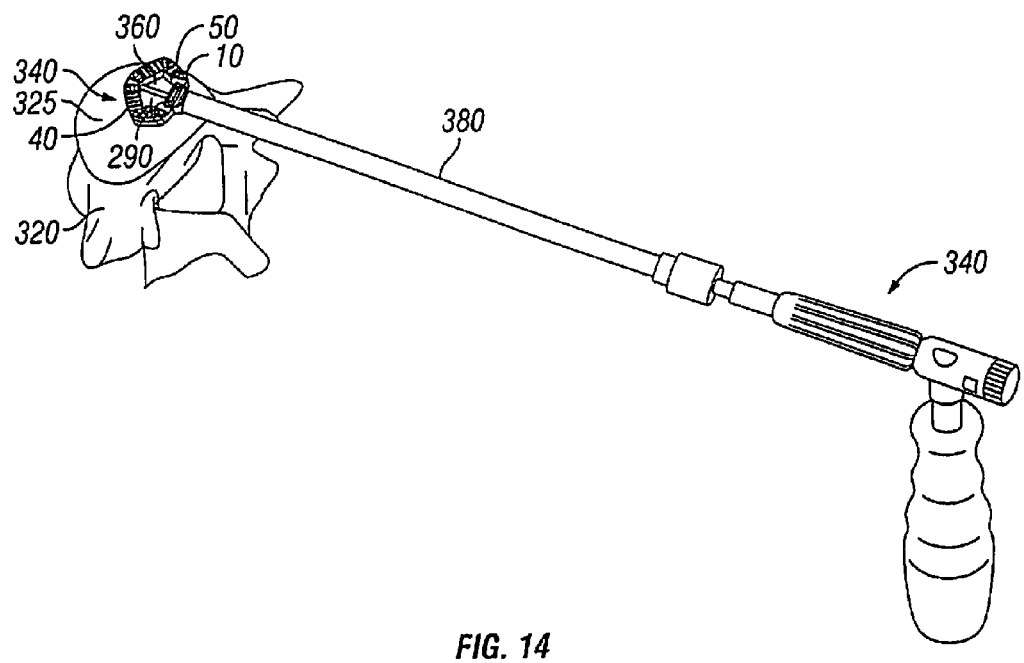
FIG. 14 is a view showing the tool of FIG. 12 expanding an expandable interbody spacer in a disc space in accordance with embodiments of the present invention.
Figure 15:
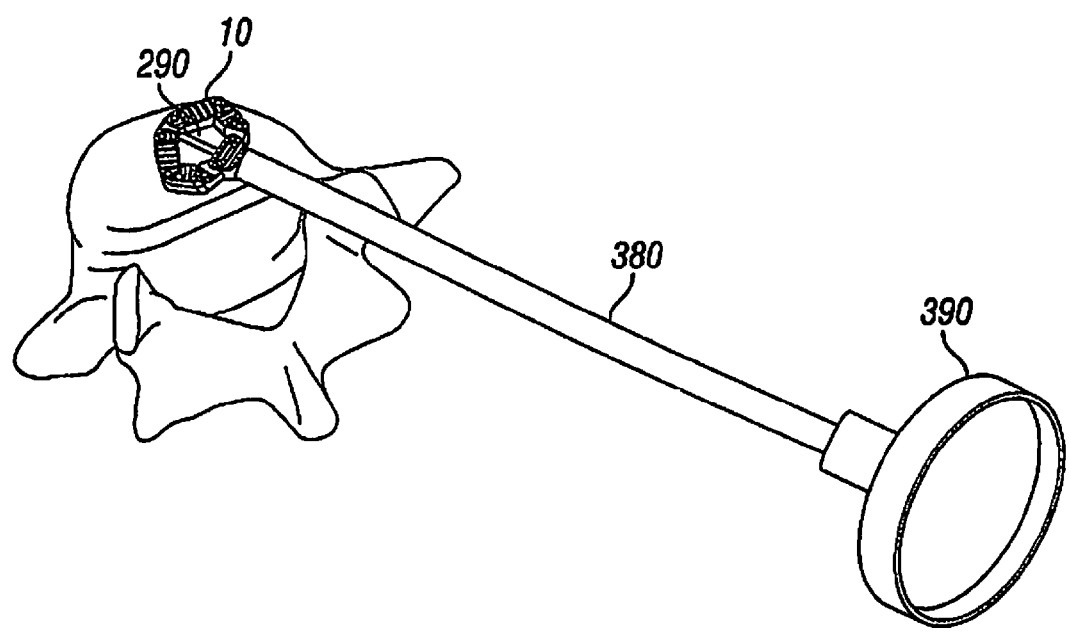
FIG. 15 is a view showing a funnel for introduction of bone-growth-inducing material into a disc space in accordance with embodiments of the present invention.

FIGS. 13 and 14 illustrate introduction of an expandable interbody spacer 10 into the disc space 330 using tool 340. For illustrative purposes, the upper vertebra 330 shown on FIG. 11 has been removed from FIGS. 13 and 14. As illustrated, the spacer 10 may be secured to the tool 340. For example, the elongated end portion 360 of the tool 340 may be disposed through the bore 270 (e.g., see FIG. 5) in the proximal connection end 60 with the distal tip 370 (e.g., see FIG. 12) of the end portion 360 secured in the opening 280 (e.g., see FIG. 5) in the distal connection end 70. As illustrated by FIG. 13, the tool 340 may introduce the spacer 10 into the disc space 330 through an access cannula 380. After introduction into the disc space 330, the spacer 10 may be laterally expanded. In accordance with present embodiments, the spacer 10 can be laterally expanded by folding the first arm 40 and the second arm 50 inward. By expanding laterally, the spacer 10 has an increased surface area contact with the endplate 325. In addition, the spacer 10 may engage harder bone around the apophyseal ring. As previously mentioned, an interior cavity 290 should be formed in the spacer 10 when in the expanded position. The tool 340 may then be detached from the spacer 10 and removed from the cannula 380. As illustrated by FIG. 15, a funnel 390 may then be placed on the cannula 380. Bone-growth inducing material may then be placed into the interior cavity 290 through the cannula 380. Because the spacer 10 has been laterally expanded, the interior cavity 290 should have a desirable amount of space for packing of the bone-growth-inducing material.

Figure 16:
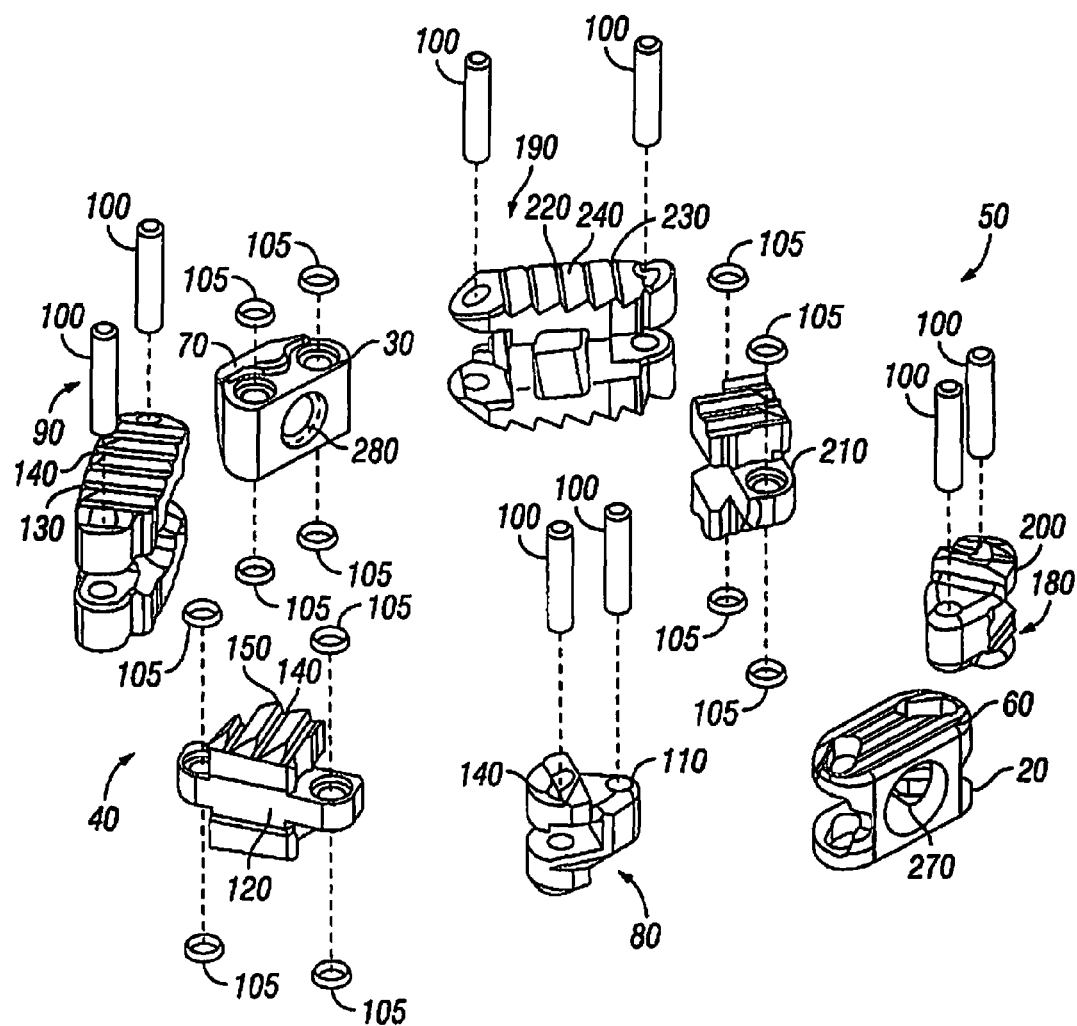
FIG. 16 is an exploded view of another embodiment of an expandable interbody spacer.

FIG. 16 illustrates an expandable interbody spacer 10 in accordance with an alternative embodiment. In the illustrated embodiment, the expandable interbody spacer 10 comprises a first jointed arm 40 and a second jointed arm 50. The first jointed arm 40 has a proximal end 80 and a distal end 90. The first jointed arm 40 comprises a plurality of links 110, 120, 130 connected end to end, for example, by pins 100. The first jointed arm 40 further may comprise washers 105 (e.g, PEEK washers) that may be disposed between the links 110, 120, 130 at their connections. The second jointed arm 50 has a proximal end 180 and a distal end 190. The second jointed arm 50 comprises a plurality of links 200, 210, 220 connected end to end, for example, by pins 100. The second jointed arm 50 further may comprise washers 105 (e.g, PEEK washers) that may be disposed between the links 200, 210, 220 at their connections. Washers 105 may also be disposed between the first arm 40 and the proximal connection member 60 and the distal connection member 70 at their respective connections. Washers 105 may also be disposed between the second arm 50 and the proximal connection member 60 and the distal connection member 70 at their respective connections. The washers 105 should have an interference fit to cause friction such that the spacer 10 may hold its shape in the entire range of the expanded implant.

Figure 18:
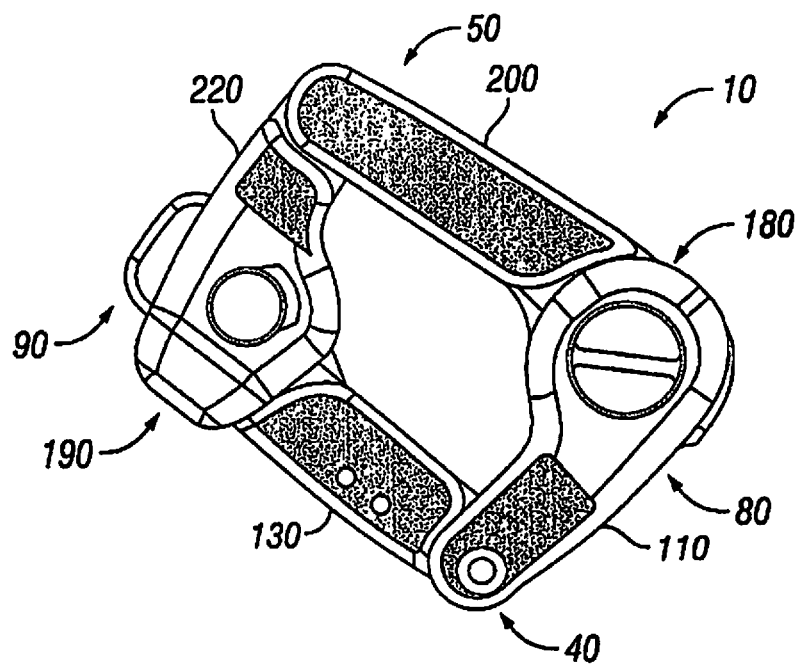
FIG. 18 is a top view of the expandable interbody spacer of FIG. 17 shown in an expanded position.
Figure 19:
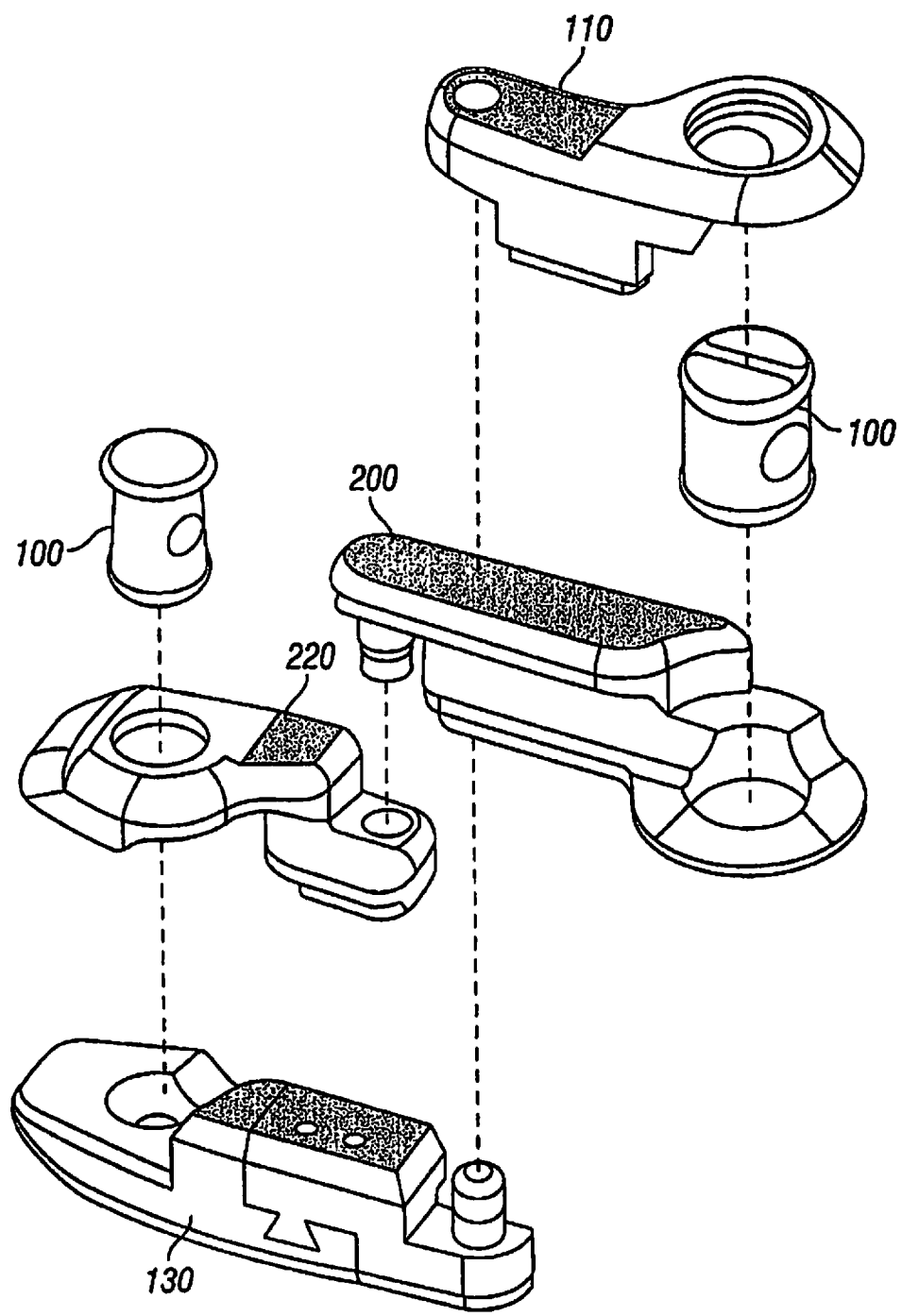
FIG. 19 is an exploded view of the expandable interbody spacer of FIG. 17.
Figure 20:
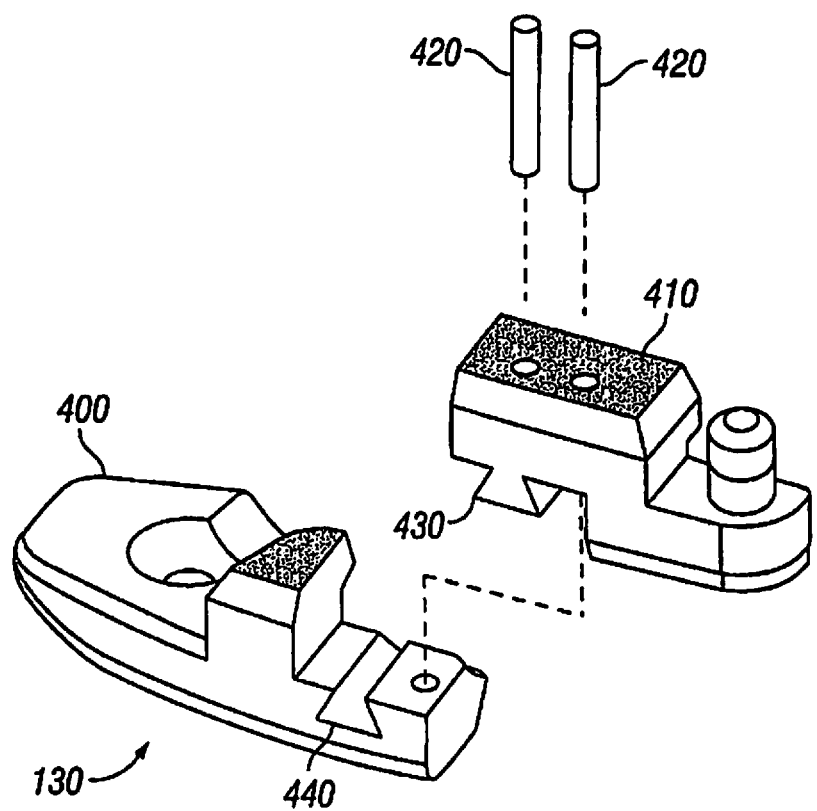
FIG. 20 is an exploded view of a link of a jointed arm of the expandable interbody spacer of FIG. 17.

The proximal ends 80, 180 may be pivotally coupled, for example, by pin 100, as shown on FIG. 19. The distal ends 90, 180 may also be pivotally coupled, for example, by pin 100, as shown on FIG. 19. The first jointed arm 40 comprises first link 110 and third link 130, the first link 110 and the third link 130 being pivotally coupled. In contrast to the first jointed arm 40 of FIGS. 1-10, there Referring now to FIGS. 17-19, an expandable interbody spacer 10 is illustrated in accordance with another embodiment of the present invention. In the illustrated embodiment, the expandable interbody spacer 10 comprises a first jointed arm 40 and a second jointed arm 50. The first jointed arm 40 has a proximal end 80 and a distal end 90. The second jointed arm 50 has a proximal end 180 and a distal end 190. The proximal ends 80, 180 may be pivotally coupled, for example, by pin 100, as shown on FIG. 19. The distal ends 90, 180 may also be pivotally coupled, for example, by pin 100, as shown on FIG. 19. The first jointed arm 40 comprises first link 110 and third link 130, the first link 110 and the third link 130 being pivotally coupled. In contrast to the first jointed arm 40 of FIGS. 1-10, there is no second link 120. As shown by FIG. 20, the third link 130 may comprise a first link segment 400 and a second link segment 410, which may be secured to one another by pins 420, for example. First link segment 400 and second link segment 410 may also have a tongue-and-groove connection, for example a groove 430 in the first link segment 400 may receive a tongue 440 of the second link segment 410. The second jointed arm comprises first link 200 and third link 220, the first link 200 and the third link 220 being pivotally coupled. In contrast to the second joint arm 50 of FIGS. 1-10, there is no second link 210.

Figure 17:
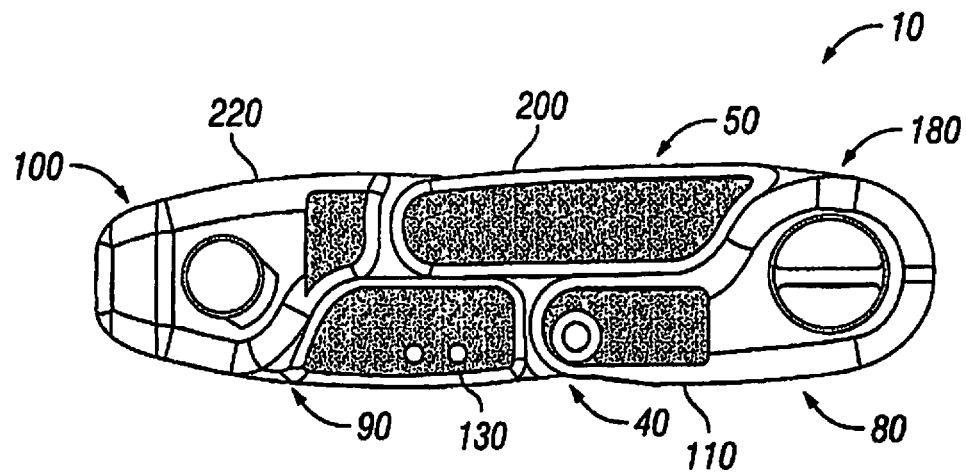
FIG. 17 is a top view of another embodiment of an expandable interbody spacer shown in a collapsed position.

In accordance with present embodiments, lateral expansion of the expandable interbody spacer 10 of FIGS. 17-19 may include folding the first arm 40 and the second arm 50 inward. For example, the proximal end 80 and the distal end 90 of the first arm 40 may be folded together, and the proximal end 180 and the distal end 190 of the second arm 50 may also be folded together.

Figure 21:
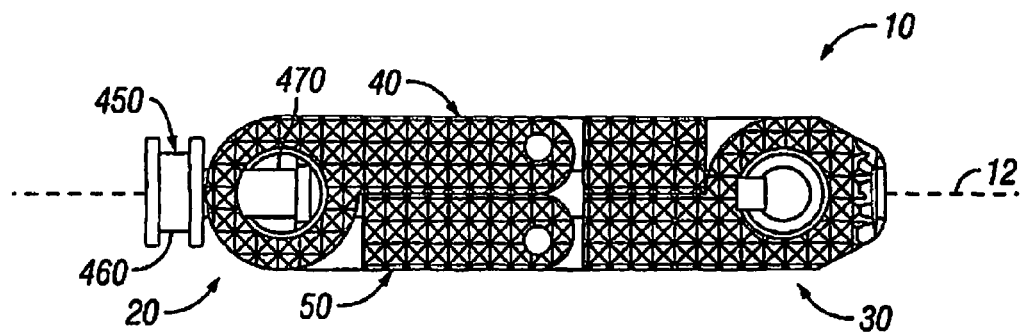
FIG. 21 is a top view of another embodiment of an expandable interbody spacer shown in a collapsed position.
Figure 22:
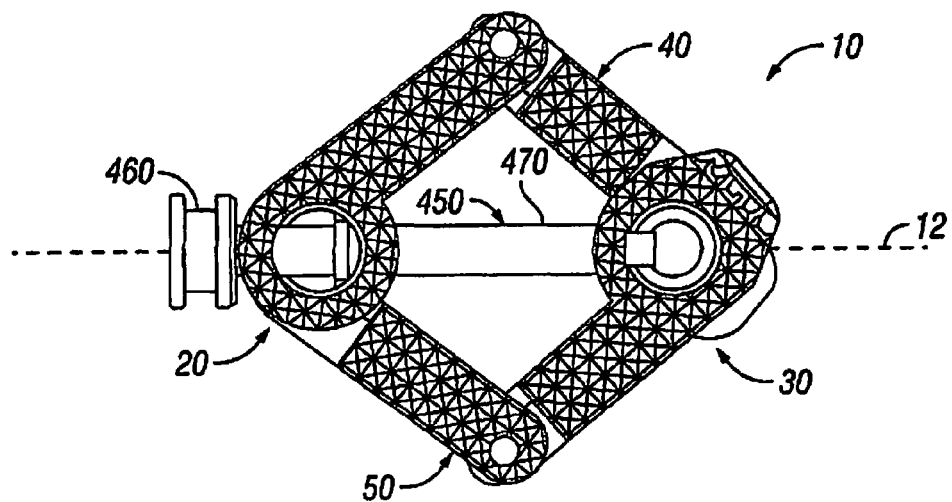
FIG. 22 is a top view of the expandable interbody spacer of FIG. 21 shown in an expanded position.

Referring now to FIGS. 21 and 22, an expandable interbody spacer 10 is illustrated in accordance with another embodiment of the present invention. In the illustrated embodiment, the expandable interbody spacer 10 has a proximal end 20 and a distal end 30. The expandable interbody spacer 10 may include a first jointed arm 40 and a second jointed arm 50 positioned on either side of longitudinal axis 12 of the spacer 10. As illustrated, the expandable interbody spacer 10 further may comprise an internal screw 450. The internal screw 450 may comprise a head 460 and an elongated body 470, which may extend generally parallel to the longitudinal axis 12 of the spacer 10. In some embodiments, the internal screw 450 may extend from the proximal end 20 to the distal end 30 of the spacer 10. In one embodiment, the elongated body 470 may be retractable. For example, the elongated body 470 may retract into the head 460, as shown on FIG. 22.

Figure 23:
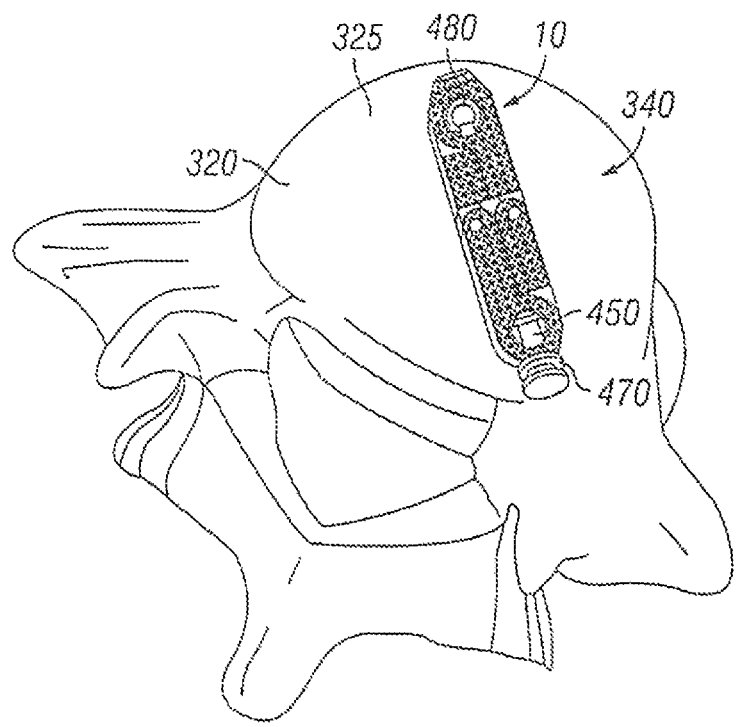
FIG. 23 is a view of the expandable interbody spacer of FIG. 21 shown in a disc space in a collapsed position.
Figure 24:
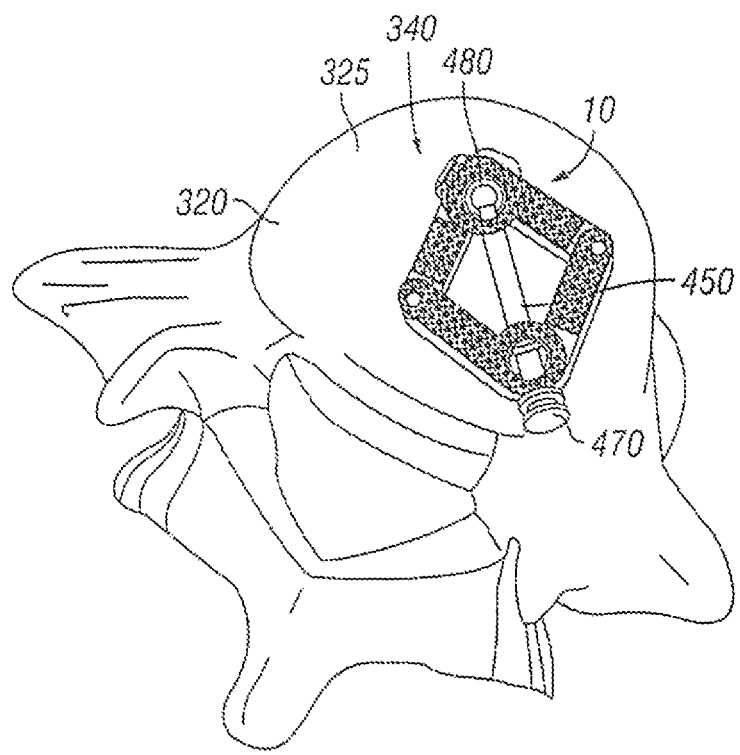
FIG. 24 is a view of the expandable interbody spacer of FIG. 21 shown in a disc space in an expanded position.

As illustrated by FIGS. 23 and 24, the spacer 10 may be introduced into the disc space 330, wherein the spacer 10 can be laterally expanded. In accordance with present embodiments, the spacer 10 can be laterally expanded by folding the first arm 40 and the second arm 50 inward. In some embodiments, the elongated body 470 may be retracted into the head 460 to cause folding of the first arm 40 and the second arm 50 inward, as the first arm 40 and the second arm 50 are secured to the distal end 480 of the internal screw 450.

Figure 25:
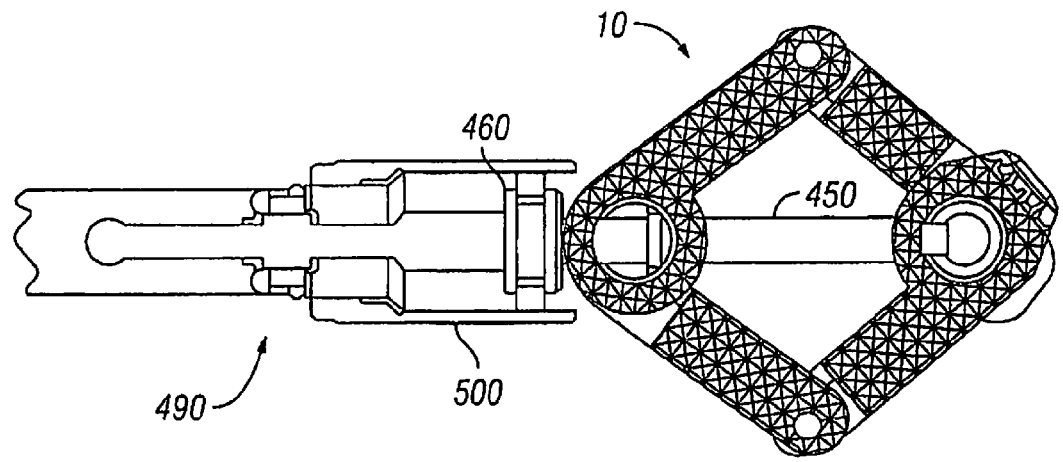
FIG. 25 is a top view of a tool shown engaging the expandable interbody spacer of FIG. 21 in accordance with embodiments of the present invention.
Figure 26:
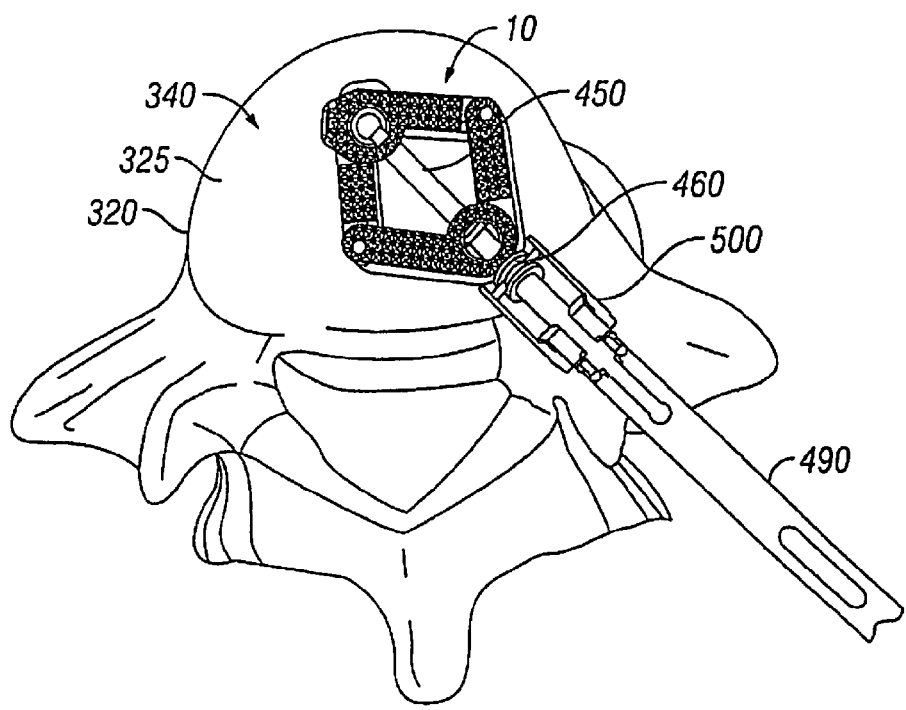
FIG. 26 is a view showing the tool of FIG. 24 expanding the expandable interbody spacer of FIG. 24 in a disc space in accordance with embodiments of the present invention.

FIG. 25 shows attachment of a tool 490 to the expandable interbody spacer 10 of FIGS. 22 and 23 in accordance with embodiments of the present invention. As illustrated, the tool 490 may have an attachment end 500, which can be secured to the head 460 of the internal screw 450. As shown by FIG. 26, the tool 40 can be used to introduce the spacer 10 into the disc space 330, wherein the spacer 10 can be laterally expanded.

While the invention herein disclosed has been described by means of specific embodiments and applications thereof, numerous modifications and variations can be made thereto by those skilled in the art without departing from the scope of the invention as set forth in the claims.

What is claimed is:

1. A surgical method comprising:
   removing at least a portion of an intervertebral disc from a disc space;
   inserting an expandable interbody spacer into the disc space; and
   expanding the expandable interbody spacer in the disc space, wherein the expandable interbody spacer comprises:
   a first jointed aim comprising a plurality of links coupled end to end;
   a second jointed arm comprising a plurality of links coupled end to end;
   a first opening formed through a first section of the expandable interbody spacer, wherein the first opening extends completely through the first section of the expandable interbody spacer;
   a second opening formed through a second section of the expandable interbody spacer, wherein the second opening is opposed to the first opening, and wherein the second opening extends only partially through the second section of the expandable interbody spacer; and an elongate body extending through the first and second openings of the expandable interbody spacer to cause expansion of the expandable interbody spacer; and wherein after expansion of the expandable spacer, the elongate body is removed from the expandable spacer.

2. The surgical method of claim 1, wherein inserting the expandable interbody spacer into the disc space is performed via a lateral approach.

3. The surgical method of claim 1, wherein inserting the expandable interbody spacer into the disc space is performed via a posterior approach.

4. The surgical method of claim 1, wherein the first opening is formed in a proximal connection member interconnecting the first jointed arm and the second jointed arm, wherein a proximal end of each of the first and second jointed arms is pivotally coupled to the proximal connection member.

5. The surgical method of claim 4, wherein the second opening is formed in a distal connection member interconnecting the first jointed arm and the second jointed arm, wherein a distal end of each of the first and second jointed arms is pivotally coupled to the distal connection member.

6. The surgical method of claim 1, wherein the first jointed arm and the second jointed arm are each configured to fold inward in opposite directions to place the expandable interbody spacer in an expanded position.

7. The surgical method of claim 1, wherein the elongate body extends from the proximal portion to the distal portion of the expandable interbody spacer.

8. The surgical method of claim 1, wherein the expandable interbody spacer has a width of about 8 mm to about 22 mm prior to expansion and a width of about 26 mm to about 42 mm after expansion.

9. The surgical method of claim 1, wherein the plurality of links of the first jointed arm comprises three links.

10. The surgical method of claim 9, wherein washers are disposed between the three links.

11. A surgical method comprising:
removing at least a portion of an intervertebral disc from a disc space;
inserting an expandable interbody spacer into the disc space; and
expanding the expandable interbody spacer in the disc space, wherein the expandable interbody spacer comprises:
a first jointed arm comprising a plurality of links;
a second jointed arm comprising a plurality of links,
a first opening formed through a first section of the expandable interbody spacer, wherein the first opening extends completely through the first section of the expandable interbody spacer; and
a second opening formed through a second section of the expandable interbody spacer, wherein the second opening is opposed to the first opening, and wherein the second opening extends only partially through the second section of the expandable interbody spacer,
wherein the first jointed arm and the second jointed arm are interconnected at a proximal portion of the expandable interbody spacer,
wherein the first jointed arm and the second jointed arm are interconnected at a distal portion of the expandable interbody spacer; and
an elongate body extending through the first and second openings of the expandable interbody spacer to cause expansion of the expandable interbody spacer,
wherein the spacer expands from a first width to a second width that is larger than the first width, and
wherein after expansion of the expandable spacer, the elongate body is removed from the expandable spacer.

12. The surgical method of claim 11, wherein removing at least a portion of an intervertebral disc comprises removing an entire intervertebral disc.

13. The surgical method of claim 11, wherein the first jointed arm comprises at least a pair of links.

14. The surgical method of claim 11, wherein inserting the expandable interbody spacer into the disc space is performed via a lateral approach.

15. The surgical method of claim 11, wherein inserting the expandable interbody spacer into the disc space is performed via a posterior approach.

16. The surgical method of claim 11, wherein the first opening is formed in a proximal connection member interconnecting the first jointed arm and the second jointed arm, wherein a proximal end of each of the first and second jointed arms is pivotally coupled to the proximal connection member.

17. The surgical method of claim 11, wherein the second width of the expandable interbody spacer is more than double the first width of the expandable interbody spacer.

18. The surgical method of claim 11, wherein the elongate body extends from the proximal portion to the distal portion of the expandable interbody spacer.

19. The surgical method of claim 18, wherein the elongate body comprises a screw having a head and a shaft.

20. The surgical method of claim 11, wherein the first opening is formed in a proximal connection member interconnecting the first jointed arm and the second jointed arm, wherein a proximal end of each of the first and second jointed arms is pivotally coupled to the proximal connection member.

* * * * *